United States Patent [19]

Weiss et al.

[11] 4,160,167

[45] Jul. 3, 1979

[54] DEVICE FOR MEASURING THE ABSORPTION OF RADIATION IN A SLICE OF A BODY

[75] Inventors: Hermann Weiss; Günter Kowalski, both of Hamburg, Fed. Rep. of Germany

[73] Assignee: U.S. Philips Corporation, New York, N.Y.

[21] Appl. No.: 796,968

[22] Filed: May 16, 1977

[30] Foreign Application Priority Data

May 19, 1976 [DE] Fed. Rep. of Germany ....... 2622177

[51] Int. Cl.² .......................... A61B 6/02; G01T 1/29
[52] U.S. Cl. ................................. 250/445 T; 250/366
[58] Field of Search ........................ 250/366, 445 T

[56] References Cited

U.S. PATENT DOCUMENTS

| 3,937,965 | 2/1976 | Vasseur | 250/366 |
| 4,047,041 | 9/1977 | Houston | 250/445 T |

Primary Examiner—Alfred E. Smith
Assistant Examiner—T. N. Grigsby
Attorney, Agent, or Firm—Thomas A. Briody; Edward J. Connors, Jr.; Jack E. Haken

[57] ABSTRACT

In third generation computer tomography apparatus, wherein radiation behind the object is measured by means of a large number of detection elements, a detection device comprises a number of detection elements which is larger than necessary for the measurement of the fan-shaped radiation beam, per se, in a direction parallel to the axis of rotation. Means are included for displacing the detection device in the direction of the axis of rotation. Detector element unbalance effects are thus averaged.

7 Claims, 3 Drawing Figures

DEVICE FOR MEASURING THE ABSORPTION OF RADIATION IN A SLICE OF A BODY

The invention relates to a device for measuring the absorption of radiation in a slice of a body, comprising a radiator for generating a fan-shaped radiation beam, which serves to irradiate the body during a measurement, and a detection device which is arranged in the radiation beam and by means of which measuring values concerning the absorption of radiation in a slice of the body can be measured. The radiator and the detection device occupy a large number of rotary positions around an axis of rotation which extends perpendicularly to the radiation and to the slice during the measurement.

A device of this kind is known from U.S. Pat. No. 3,937,963. The detection device described therein consists of a number of detection elements which are arranged on an arc or a straight line which extends through the slice in the plane. The advantage of such a device over a device comprising only a single detection element (for example, as described in U.S. Pat. No. 3,778,614) is that the measurement can be executed faster, because a large number of measuring values can be simultaneously obtained and because it is only necessary to rotate the assembly formed by the radiator and the detection device around the axis. On the other hand, this device has the drawback that, due to the different sensitivities of detection elements in the detection device, errors may occur which become apparent during the reconstruction of the absorption of the slice of the body, notably in the region of the centre of rotation.

In the German Offenlegungsschrift No. 25 03 978 a device is described in which these reconstruction errors are reduced or eliminated. During a measurement the radiator/detection device assembly of this device first performs a full revolution. The detection elements measure the absorption of the body along the same strip through the body at the beginning and at the end of this revolution. If the output signals of the individual detection elements deviate from each other, the extent of the temporary change of the sensitivity can be measured on the basis thereof. Subsequently, the detection elements are rotated about the centre of curvature of the arc of the circle on which they are arranged, so that each detection element measures, during a subsequent second revolution, the absorption along strips through the body wherealong the absorption has been measured by one of the two adjoining detection elements during the previous measurements. When the measuring values produced by a detection element during the second revolution are compared with the measuring values produced by the adjoining detection element during the first revolution differences in the sensitivity of adjoining detection elements can be derived and used for correcting the measuring values. Subsequently, the detection elements are returned to the position occupied during the first measurement, after which the system formed by the radiator and the detection device performs a third revolution and the absorption is measured again. The measuring values thus obtained are used to calculate (by comparison with the measuring values obtained during the second revolution) differences in the sensitivity of adjoining detection elements and also (by comparison of the measuring values obtained at the beginning and at the end of the revolution) fluctuations in the sensitivity of the individual detection elements.

The method carried out with such a device is thus based on the repeated measurement of the absorption along each strip through the body. As a result, the measuring time is prolonged and the radiation dose applied to the body is also increased. A further drawback of the known device is that the measuring values change if the position of the body to be examined changes during the measurement. The changed measuring values are incorrectly interpreted by the device as a different sensitivity of adjoining detection elements or as drift of the sensitivity of the individual detection elements, so that additional errors occur in the reconstruction of the absorption in the slice.

The invention deals with the problem of avoiding or reducing reconstruction errors in a device comprising a radiator and a large number of detection elements; however, a primary object is to avoid or eliminate errors which arise to an increased extent in the vicinity of the centre of rotation of the radiator/detection device assembly (this centre of rotation is usually situated in the slice of the body to be examined) and which are particularly significant. These reconstruction errors are also caused by the different sensitivities of the individual detection elements. Thus, the invention has for its object to avoid or at least mitigate reconstruction errors in the vicinity of the centre of rotation of the assembly formed by the radiator and the detection device, without increasing the measuring time or the dose applied to the patient. As a result of a comparatively short mesuring period, movement of the body during the measurement being avoided.

The device in accordance with the invention is characterized in that the detection device comprises, at least for measuring the absorption in and in the vicinity of a centre of rotation of the radiator and the detection device, a series of detection elements in a direction parallel to the axis of rotation, the length of the said series being larger than the thickness of the fan-shaped radiation beam and the device further comprises displacement means for displacing the series of detection elements during the measurement in a direction parallel to the axis of rotation. The detection device may consist of individual detection elements, each of which comprises a separate output. Alternatively, it may be a detection device whose elements do not have separate outputs but which instead store a value which is dependent of the intensity of the incident radiation, the values stored being consecutively read. A detection device of this kind consists, for example, of an image intensifier and a television camera which is connected thereto.

A further embodiment of the device in accordance with the invention is characterized in that the detection device comprises a rectangular matrix of discrete detection elements which are arranged in a direction parallel to the axis of rotation as well as in a direction perpendicular thereto. All series of detection elements are displaceable at the same speed during the measurement in a direction parallel to the axis of rotation.

If the reconstruction in the region of the centre of rotation is to be substantially improved, a large number of detectors is required.

A further preferred embodiment in accordance with the invention, comprising a smaller number of individual detection elements, is characterized in that the detection device comprises a number of series of detection elements which extend parallel to the axis of rotation and which are displaceable at a different speed parallel to the axis of rotation, the speed being highest in the centre. In the above embodiment of the device in accordance with the invention, the series of detection elements need comprise only a few individual detection elements or only a single detection element at the edges of the fan-shaped radiation beam (the speed of this "series" of one detection element in a direction parallel to the axis of rotation equals zero in this case). In the centre, however, the detection device must comprise a series including a comparatively large number of detection elements, because the centre of the detection device always measures the absorption of the same part of the body examined (i.e. the part in the region of the centre of rotation).

A further embodiment of the device in accordance with the invention is characterized in that the detection device comprises an image intensifier which is displaceable, parallel to the axis of rotation, relative to the radiation beam. The output image of the image intensifier may then be converted into an electric signal, for example, by means of a television camera, the video signal being a measure for the intensity of the radiation incident on the entrance screen of the image intensifier and hence of the absorption of the body. However, instead of a television camera, use can also be made of a photodiode matrix.

A further embodiment of the device in accordance with the invention is characterized in that an angle which is enclosed by the detection device in a direction perpendicular to the axis of rotation is larger than the angle enclosed by the fan-shaped radiation beam, the detection device being displaceable in the direction perpendicular to the axis of rotation during the measurement. A shift of the detection device in this direction has already been proposed in a co-pending patent application Ser. No. 756,856 filed Jan. 5, 1977. During the subsequent reconstruction of the absorption distribution, however, the fact must be taken into account that each detection element changes its position within the fan-shaped radiation beam during a measurement.

A further embodiment yet of the device in accordance with the invention is characterized in that the detection device is rotated during the measurement. A small improvement in the reconstruction accuracy in the centre of rotation would already occur if the detection device were exclusively rotated (without translatory displacement of the detection device parallel to the axis of rotation and/or perpendicularly thereto). However, it is essential that the detection device changes its position during the measurement relative to the fan-shaped radiation beam, mainly in a plane which is perpendicular to the fan-shaped radiation beam.

Figure 1:
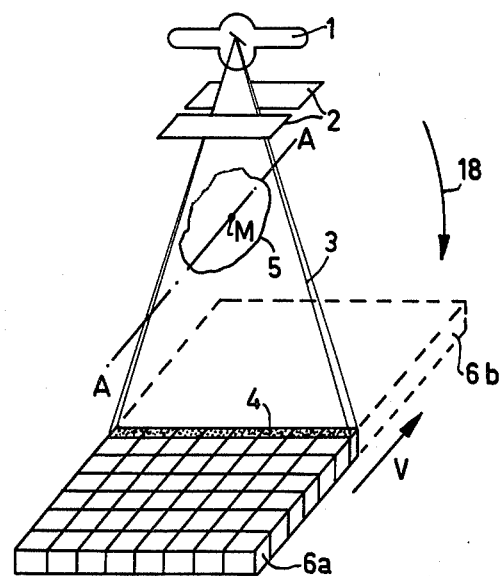
FIG. 1 shows a first embodiment in which a detection device consists of individual detection elements.

The reference numeral 1 in FIG. 1 denotes a radiation source which emits gamma or X-radiation, for example, an X-ray tube. A radiation beam 3 is stopped to a flat and fan-shape by an aperture 2. The said radiation beam passes through a body 5 and irradiates a small strip 4 on a detection device 6a. During the measurement, the radiator 1 and the device 6a are rotated, together with the aperture 2, about an axis A—A, as indicated by the arrow 18. The intersection of the said axis with the fan-shaped radiation beam 3, denoted by M, generally is situated within the body 5. The device described thus far is known (see, for example, U.S. Pat. No. 3,937,963 which also discloses detailed information as regards the mechanical construction).

However, while in the known apparatus the dimensions of the detection device corresponds approximately to the dimensions of the strip 4, so that the detection device can exactly enclose the fan-shaped radiation beam 3, in accordance with the invention the detection device 6a is substantially wider. To this end, a large number of individual detection elements are arranged in a rectangle in the detection device 6a, so that there are a large number of rows and columns which extend both parallel and perpendicular to the axis A—A, each column having a length such that it can completely cover the strip 4 of the fan-shaped radiation beam 3. During the measurement, (i.e. also during the rotation of the radiator 1 and the detection device 6a as denoted by the arrow 18) the detection device 6a is shifted parallel to the direction of the axis A—A.

As a result of this shift, the radiation intensity of the fan-shaped radiation beam 3 is measured by different detection elements each time. This benefits the reconstruction of the absorption distribution, notably in the region of the centre of rotation M, because the radiation in this region is then measured by not only one or only a few detection elements, as would be the case if the detection device 6a was not displaced during the measurement. During the reconstruction of the radiation absorption the various sensitivities of the detection elements are summed in the region of the centre of rotation and produce a substantial reduction of the reconstruction error in the vicinity of the centre of rotation M (because the mutual deviations of the sensitivities of the detection elements generally at least partly cancel each other).

The (linear) motion of the detection device 6a in a direction parallel to the axis of rotation A—A may be coupled, via a drive, to a rotary drive which rotates the radiator 1, the aperture 2 and the detection device 6a about the axis of rotation. When, for example, use is made of step motors for the rotary movement a separate step motor drive for driving the detection device can be used and the step pulses applied to the latter motor can also be applied to the step motor for realizing the rotary movement.

Each part of the fan-shaped radiation beam 3 is associated with a given series of detection elements (extending parallel to the axis of rotation) in the matrix-shaped detection device 6a, i.e. the intensity in the relevant part of the fan-shaped radiation beam 3 is measured only by the detection elements of this series. In order to obtain the measuring value associated with a given part of the fan-shaped radiation beam 3, the output signals of the detection elements of a single series need only be added. The dark currents of the detection elements of a series which are situated outside the radiation beam 3 are then also added thereto.

In order to reduce, if necessary, the effect of these dark currents, it is possible to determine, in dependence of the position of the detection device 6a relative to the radiation beam 3, the detection element or elements of a detector series which are situated in the radiation beam during the relevant phase of the measurement, and to only use the output signals thereof for forming a measuring value during the relevant phase of the measurement. The detection elements which are effective during a given phase of the measurement are situated in a column of the matrix-shaped detection device 6a which extends perpendicularly to the axis of rotation A—A.

For statistical reasons, a substantial reduction of the reconstruction error, notably in the centre of rotation, can be achieved only if the radiation in this region is consecutively measured by a substantial number of detection elements, i.e. the number of columns of the matrix-shaped detection device 6a must be comparatively large, for example, 50. The number of series of the detection device which extend parallel to the axis of rotation must also be substantially larger than shown in the drawing, because this number corresponds to the number of detection elements irradiated during a phase of the measurement, the said number being decisive for the spatial resolution. This number lies in the order of magnitude of 100–200. A detection device 6a as shown in FIG. 1 thus comprises a large number of individual detection elements, which may make the device very expensive.

Figure 2:
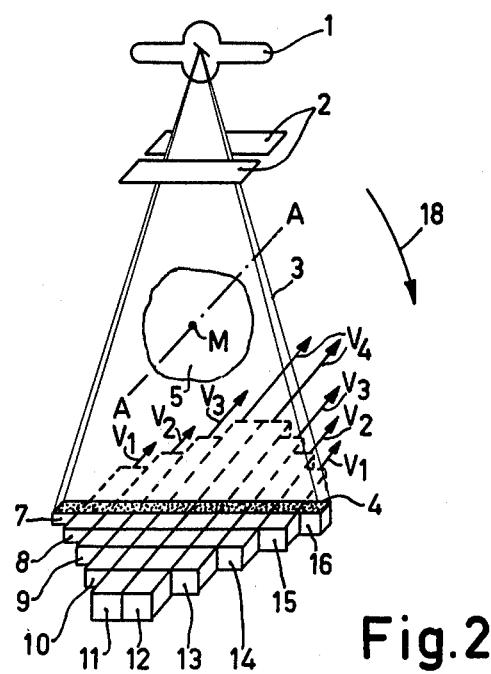
FIG. 2 shows a further embodiment which also comprises discrete detection elements.

FIG. 2 shows a less expensive device, comprising a smaller number of detection elements, in which the improvement of the reconstruction, notably in the centre of rotation, is not reduced or is not substantially reduced. This embodiment corresponds mainly to that shown in FIG. 1. The detection device shown in FIG. 2 deviates from that shown in FIG. 1 in the following respects:

(a) Successive series of detection elements which extend parallel to the axis of rotation A—A comprise numbers of detection elements. The series 11 and 12, measuring the radiation in the region of the centre of rotation, comprise the largest number of detection elements, while the series 13, 14, 15, 16 and 10, 9, 8, 7 comprise progressively less detection elements as the distance from the centre increases.

(b) During the measurement successive series of detection elements are displaced in the direction parallel to the axis of rotation at a different speeds, so that in the course of the measurement all detection elements in each series intercept the radiation beam 3. As a result, the speed of the central series 11 and 12, denoted by an arrow $V_4$, is highest, while the speeds $V_1$, $V_2$, $V_3$ of the other series 13, 14, 15 and 10, 9, 8, respectively, is correspondingly lower. Because "series" 7 and 16 consists of only a single detection element, no displacement takes place.

This embodiment is based on the recognition of the fact that, in the known apparatus of the kind set forth, the reconstruction errors are caused mainly by (mutual) deviations of the detection elements which measure the radiation behind the centre of rotation, i.e. the detection elements which measure the radiation of the central region of the radiation beam 3. These detection elements are "associated" with a given fixed region of the slice examined, (i.e. the region around the centre of rotation M) while the regions which are situated further from the centre of rotation M are "associated" with a larger number of detection elements. Therefore, for the improvement of the reconstruction accuracy it is of essential importance that the radiation in the region behind the centre of rotation M or behind the axis of rotation A—A is measured by a larger number of detection elements, thus the central series 11 and 12 of the embodiment shown in FIG. 2 comprise a very large number of detection elements.

In practice it is sufficient that only a few series in the centre to comprise a larger number of detection elements, while all other series consist of only a single detection element, like the "series" 7 and 16 in FIG. 2. If the central series comprise an equal number of detection elements, they can be displaced together at the same speed, while the "series" which are situated further outwards and which comprise only one detection element need not be displaced.

Figure 3:
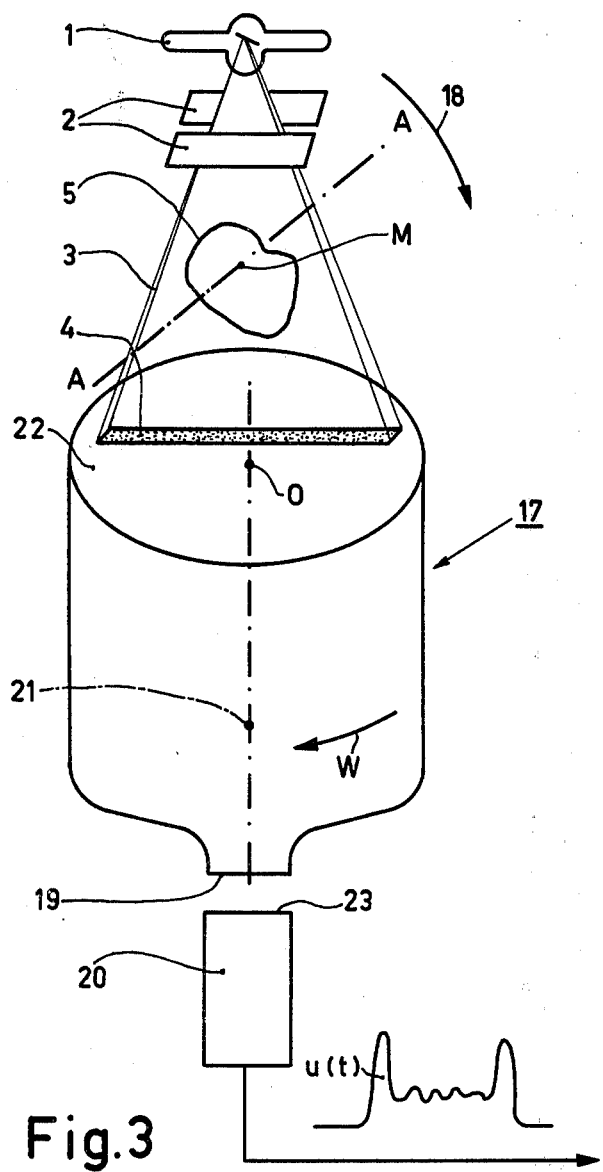
FIG. 3 shows an embodiment in which the detection device comprises an image intensifier.

The detection embodiment of the device which is diagrammatically shown in FIG. 3 utilizes an image intensifier 17. A strip 4 on the entrance screen 22 of the image intensifier 17 is irradiated by the fan-shaped radiation beam 3. An image of the strip 4 then appears on the output screen 19 of the image intensifier 17 with an increased intensity. A television camera tube 20 picks up the image formed on the output screen 19. The image is read by a scanning electron beam having a width approximately equal to the width of the strip on the photosensitive layer of the television camera tube 20, the scanning electron beam being deflected in the longitudinal direction of this image. The variation of the output signal u(t) of the television camera tube 20 then represents the variation of the radiation intensity behind the object 5 along the strip 4 (for a given phase of the measurement), so that on the basis of the amplitude of the output signal u(t) the absorption of the X-radiation by the object 5 in a given position can be measured at a given instant. In accordance with the invention, while the radiator 1 and the image intensifier 17 are rotated, together with the aperture 2, about the axis A—A which extends perpendicularly to the plane of the drawing and through the centre of rotation M, the image intensifier 17 is rotated about a symmetry axis 21 as denoted by the arrow W. When the strip 4 is then situated outside the point of intersection 0 of the symmetry axis or the axis of rotation 21 and the entrance screen 22 of the image intensifier 17, the strip 4 performs a movement relative to the radiation-sensitive entrance screen 22 which may be sub-divided into three components: the movement parallel to the axis of rotation A—A of the radiator 1 and the image intensifier 17, a component perpendicular thereto, i.e. in the longitudinal direction of the strip 4, and a pure rotary component. The movement of the effective measuring surface of a detection device in the longitudinal direction of the strip has already been proposed in co-pending Patent Application Ser. No. 756,856, wherein it is described for a detection device consisting of discrete detection elements.

As a result of the rotation of the image intensifier 17 about its symmetry axis 21 the absorption in each point of the plane of examination 5 and in each part of the fan-shaped radiation beam 3 is converted into visible light by different surface elements of the entrance screen 22, with the result that the said reconstruction errors are reduced notably in the centre of rotation M. If only the image intensifier 17 is rotated, the image of the strip 4 appears on the entrance screen 23 of the television camera tube 20 in the same position each time. The television camera tube 20 need not be specially rotated. The deflection voltages thereof should not be changed. However, if the television camera tube 20 is rotated, each point of the surface of the entrance screen 22 of the image intensifier 17 is each time assigned to new points on the photosensitive layer of the television camera tube during the measurement, so that the effect of fluctuations of the sensitivity of the surface of the entrance screen 22, of the image intensifier 17 as well as of the photosensitive layer of the television camera tube 20 on the reconstruction accuracy is reduced.

Instead of a rotary movement, the image intensifier 17 can also perform a movement parallel to the axis of rotation A—A of the radiator 1 and the amplifier 17 during the measurement. However, either the deflection voltage on the television camera tube 20 must then be changed or the television camera tube 20 may not be moved. In the former case, however, each point of the surface of the entrance 22 of the image intensifier 17 is always assigned to the same point of the photosensitive layer of the television camera tube 20, so that the said effect on the reconstruction accuracy is cancelled.

It is alternatively possible to rotate the image intensifier 17 during a measurement about an axis which is not identical to the symmetry axis 21 but which extends parallel thereto. In that case it is effective to rotate the television camera tube 20 about the same axis.

The described invention enables the use of a great variety of detection elements such as, for example, gas proportional counters, scintillators, image intensifiers with electronic scanning by a television camera, image intensifiers comprising a photodiode matrix and many others.

What is claimed is:

1. A device for measuring the absorption of radiation in a slice of a body, comprising a radiator means for generating a fan-shaped radiation beam which irradiates the body during a measurement, and a detection device which is disposed in the radiation beam and which measures measuring values describing the absorption of radiation in the slice of the body, the radiator and the detection device occupying a large number of rotary positions around an axis of rotation which extends perpendicularly to the radiation and the slice during the measurement, wherein the detection device comprises a series of detection elements disposed in a direction parallel to the axis of rotation, the length of the said series being larger than the thickness of the fan-shaped radiation beam, and further comprising displacement means for displacing the series during the measurement in a direction parallel to the axis 2. A device as claimed in claim 1, wherein the detection device comprises a rectangular matrix of discrete detection elements which are disposed in a direction parallel to the axis of rotation as well as in a direction perpendicular thereto, all of the detection elements being displaceable, during the measurement, at the same speed and parallel to the axis of rotation.

3. A device as claimed in claim 1, wherein the detection device comprises a number of series of detection elements which extend parallel to the axis of rotation and which are displaceable parallel to the axis of rotation at different speeds, the speed of series in the center of the device being highest.

4. A device as claimed in claim 1, wherein the detection device comprises an image intensifier which is displaceable parallel to the axis of rotation.

5. A device as claimed in claim 1 wherein the angle subtended by the detection device in a direction perpendicular to the axis of rotation is larger than the angle enclosed by the fan-shaped radiation beam and the detection device is displaceable in the direction perpendicular to the axis of rotation during the measurement.

6. A device as claimed in claim 1, wherein the detection device is rotated during the measurement.

7. A device as claimed in claim 4, wherein the detection device is rotated during the measurement.

* * * * *